(12) United States Patent  
Plaven (10) Patent No.: US 9,368,004 B2  
(45) Date of Patent: Jun. 14, 2016

(54) BATTERY-POWERED SURGICAL DEVICES INCLUDING INTERNALLY-MOUNTED VISUAL INDICATORS

(71) Applicant: COVIDIEN LP, Mansfield, MA (US)

(72) Inventor: Thomas Plaven, Littleton, CO (US)

(73) Assignee: COVIDIEN LP, Mansfield, MA (US)

(*) Notice: Subject to any disclaimer, the term of this patent is extended or adjusted under 35 U.S.C. 154(b) by 241 days.

(21) Appl. No.: 14/050,593

(22) Filed: Oct. 10, 2013

(65) Prior Publication Data

US 2014/0104070 A1    Apr. 17, 2014

Related U.S. Application Data

(60) Provisional application No. 61/715,061, filed on Oct. 17, 2012.

(51) Int. Cl.

| G08B 5/00 | (2006.01) |
|---|---|
| G08B 5/36 | (2006.01) |
| A61B 17/32 | (2006.01) |
| A61B 18/14 | (2006.01) |
| A61B 17/00 | (2006.01) |
| A61B 19/00 | (2006.01) |
| A61B 18/00 | (2006.01) |

(52) U.S. Cl.
CPC .......... *G08B 5/36* (2013.01); *A61B 17/320092* (2013.01); *A61B 18/1445* (2013.01); *A61B 2017/00734* (2013.01); *A61B 2018/0063* (2013.01); *A61B 2018/0091* (2013.01); *A61B 2018/1455* (2013.01); *A61B 2019/4836* (2013.01); *A61B 2019/5219* (2013.01)

(58) Field of Classification Search
CPC ............................... H02J 7/0052; H02J 7/025
USPC ................. 340/815.45, 693.5, 691.1, 815.76; 362/23.9, 23.12, 23.14, 555, 119, 120, 362/296, 347
See application file for complete search history.

(56) References Cited

U.S. PATENT DOCUMENTS

| 6,776,499 | B2* | 8/2004 | Chang ........................... 362/119 |
|---|---|---|---|
| 6,819,506 | B1* | 11/2004 | Taylor et al. .................. 359/726 |
| 7,534,002 | B2* | 5/2009 | Yamaguchi et al. ............ 362/84 |
| 7,670,030 | B2* | 3/2010 | Klipstein ....................... 362/304 |
| 2004/0062047 | A1* | 4/2004 | Camarota et al. ............. 362/399 |
| 2004/0067038 | A1* | 4/2004 | Popovic ............... G02B 6/0041 385/146 |
| 2005/0047114 | A1* | 3/2005 | Harrell et al. ................. 362/101 |
| 2006/0012299 | A1* | 1/2006 | Suehiro et al. ................ 313/512 |
| 2007/0126994 | A1* | 6/2007 | Hwang ................ G02B 6/0046 353/94 |
| 2007/0224571 | A1* | 9/2007 | Watson ........................... 433/31 |
| 2008/0049445 | A1* | 2/2008 | Harbers ................. G02B 6/002 362/612 |
| 2009/0116243 | A1* | 5/2009 | Condon et al. ................ 362/294 |
| 2010/0008082 | A1* | 1/2010 | Brass et al. .................... 362/202 |
| 2011/0141731 | A1* | 6/2011 | Chang .................... F21V 7/0008 362/235 |
| 2011/0235313 | A1* | 9/2011 | Canella ......................... 362/157 |
| 2012/0033411 | A1* | 2/2012 | Heo .............................. 362/108 |
| 2012/0179159 | A1* | 7/2012 | Krapohl ................ H02J 7/0042 606/41 |

(Continued)

*Primary Examiner* — Ojiako Nwugo (57) ABSTRACT

An assembly for use with a surgical device includes an enclosure defining a passageway extending from an interior to an exterior thereof and a visual indicator mounted within the interior of the enclosure adjacent the passageway. The visual indicator is configured to emit light. The passageway is partially defined by a concave surface of the enclosure and/or a chamfered portion of the enclosure to facilitate the passage of light emitted by the visual indicator through the passageway and to the exterior of the enclosure to increase the external viewing angle of the light emitted from the visual indicator.

20 Claims, 6 Drawing Sheets

(56) References Cited

U.S. PATENT DOCUMENTS

| | | | |
|---|---|---|---|
| 2013/0049041 A1* | 2/2013 | Ramer et al. | 257/98 |
| 2013/0128496 A1* | 5/2013 | Chien et al. | 362/95 |
| 2013/0170216 A1* | 7/2013 | Li | F21V 5/04 |
| | | | 362/277 |
| 2014/0309499 A1* | 10/2014 | Swift | 600/214 |
| 2014/0338504 A1* | 11/2014 | Beer et al. | 81/57.39 |

\* cited by examiner

BATTERY-POWERED SURGICAL DEVICES INCLUDING INTERNALLY-MOUNTED VISUAL INDICATORS

CROSS REFERENCE TO RELATED APPLICATION

The present application claims the benefit of and priority to U.S. Provisional Application Ser. No. 61/715,061, filed on Oct. 17, 2012, the entire contents of which are incorporated herein by reference.

BACKGROUND

1. Technical Field

The present disclosure relates to battery-powered devices, and, more particularly, to battery-powered devices including internally mounted visual indicators, e.g., LED's or other light sources, for visually indicating to a user characteristics and/or conditions of the device.

2. Background of Related Art

Battery-powered devices, e.g., power tools, electronics, powered surgical instruments, etc., are widely used in many different fields. Many of these battery-powered devices incorporate one or more visual indicators, e.g., LEDs or other light sources, that visually indicate to the user characteristics and/or conditions of the device. For example, by turning the indicator(s) on/off, setting the indicator(s) to output a particular color, setting the indicator(s) to output at a particular brightness, and/or blinking the indicator(s), various different characteristics and/or conditions can be communicated to the user. As can be appreciated, the more easily the user can visualize the indicator(s), the more readily the user is able to ascertain the characteristics and/or conditions that are indicated.

Some battery-powered devices require significant enclosures surrounding the internal electronics of the device, e.g., to protect the internal electronics, inhibit interference, provide insulation, etc. Battery-powered surgical instruments, for example, typically include sealed enclosures surrounding the power generation and control electronics to provide protection, inhibit moisture from reaching the power generation and control electronics, and function as a heat sink to absorb heat produced by the power generation and control electronics. In such and similar configurations, since the indicator(s), which is mounted on the power generation and control electronics, is internally mounted, or "buried" within the enclosure, visualization of the indicator(s) may be limited.

SUMMARY

In accordance with the present disclosure, an assembly for use with a surgical device is provided. The assembly includes an enclosure defining a passageway extending from an interior to an exterior thereof and a visual indicator mounted within the interior of the enclosure adjacent the passageway. The visual indicator is configured to emit light. The passageway is partially defined by a concave surface of the enclosure and/or a chamfered portion of the enclosure to facilitate the passage of light emitted by the visual indicator through the passageway and to the exterior of the enclosure to increase the external viewing angle of the light emitted from the visual indicator.

In aspects, the assembly further includes an outer housing disposed about the enclosure. The outer housing includes an aperture positioned adjacent the passageway to permit passage of light emitted by the visual indicator therethrough for visualization from an exterior of the outer housing.

In aspects, a lens is disposed within the aperture of the outer housing. The light emitted by the visual indicator is configured for passage through the lens for visualization from the exterior of the outer housing.

In aspects, the visual indicator is an LED.

In aspects, electronic circuitry is mounted within the interior of the enclosure. The visual indicator is mounted on the electronic circuitry.

In aspects, the electronic circuitry is disposed on a printed circuit board.

In aspects, the enclosure functions as a heat sink to absorb heat emitted by the electronic circuitry.

In aspects, the passageway is partially defined by one or more concave surfaces of the enclosure and one or more chamfered portions of the enclosure.

In aspects, a thickness of the enclosure is about three or more times greater than a narrow width of the passageway.

In aspects, the visual indicator is displaced from the exterior of the enclosure a distance that is about three or more times greater than a narrow width of the passageway.

Also provided in accordance with the present disclosure is an assembly for use with a surgical device including an outer housing defining a first aperture extending therethrough and an inner enclosure defining a second aperture therethrough. The first and second apertures cooperate to define a passageway extending from an interior of the inner enclosure to an exterior of the outer housing. A visual indicator is mounted within the interior of the inner enclosure adjacent the passageway. The visual indicator is configured to emit light. The passageway is partially defined by a concave surface of the inner enclosure and/or a chamfered portion of the inner enclosure to facilitate the passage of light emitted by the visual indicator through the passageway and to the exterior of the outer housing to increase the external viewing angle of the light emitted from the visual indicator.

In aspects, a lens is disposed within the aperture of the outer housing. The light emitted by the visual indicator is configured for passage through the lens for visualization from the exterior of the outer housing.

In aspects, the visual indicator is an LED.

In aspects, electronic circuitry is mounted within the interior of the inner enclosure. The visual indicator is mounted on the electronic circuitry.

In aspects, the inner enclosure functions as a heat sink to absorb heat emitted by the electronic circuitry.

In aspects, the outer housing functions as a moisture barrier to inhibit moisture from reaching the electronic circuitry.

In aspects, the passageway is partially defined by one or more concave surfaces of the inner enclosure and/or one or more chamfered portions of the inner enclosure.

In aspects, a combined thickness of the inner enclosure and outer housing is about three or more times greater than a narrow width of the passageway.

In aspects, the visual indicator is displaced from the exterior of the outer housing a distance that is about three or more times greater than a narrow width of the passageway.

In aspects, the external viewing angle of the light emitted from the visual indicator in a direction of the narrow width of the passageway is at least about 170 degrees.

BRIEF DESCRIPTION OF THE DRAWINGS

Various aspects of the present disclosure are described hereinbelow with reference to the drawings, wherein.

DETAILED DESCRIPTION

The present disclosure allows for a greater degree of visualization of visual indicators, e.g., LED's, mounted within battery-powered devices. For example, the features and aspects of the present disclosure allow for a greater degree of visualization of an LED mounted on the power generation and control electronics of a surgical instrument by channeling light emitted from the LED through the enclosure and outer housing of the surgical instrument, and ultimately through an LED lens so as to maximize the viewing angle(s) from which the LED light is viewable from the exterior of the instrument. However, although the present disclosure is primarily described hereinbelow with respect to battery-powered surgical instruments, it is contemplated that the present disclosure be equally applicable for channeling light emitted from any internally mounted visual indicator so as to provide a greater degree of visualization thereof.

Figure 1:
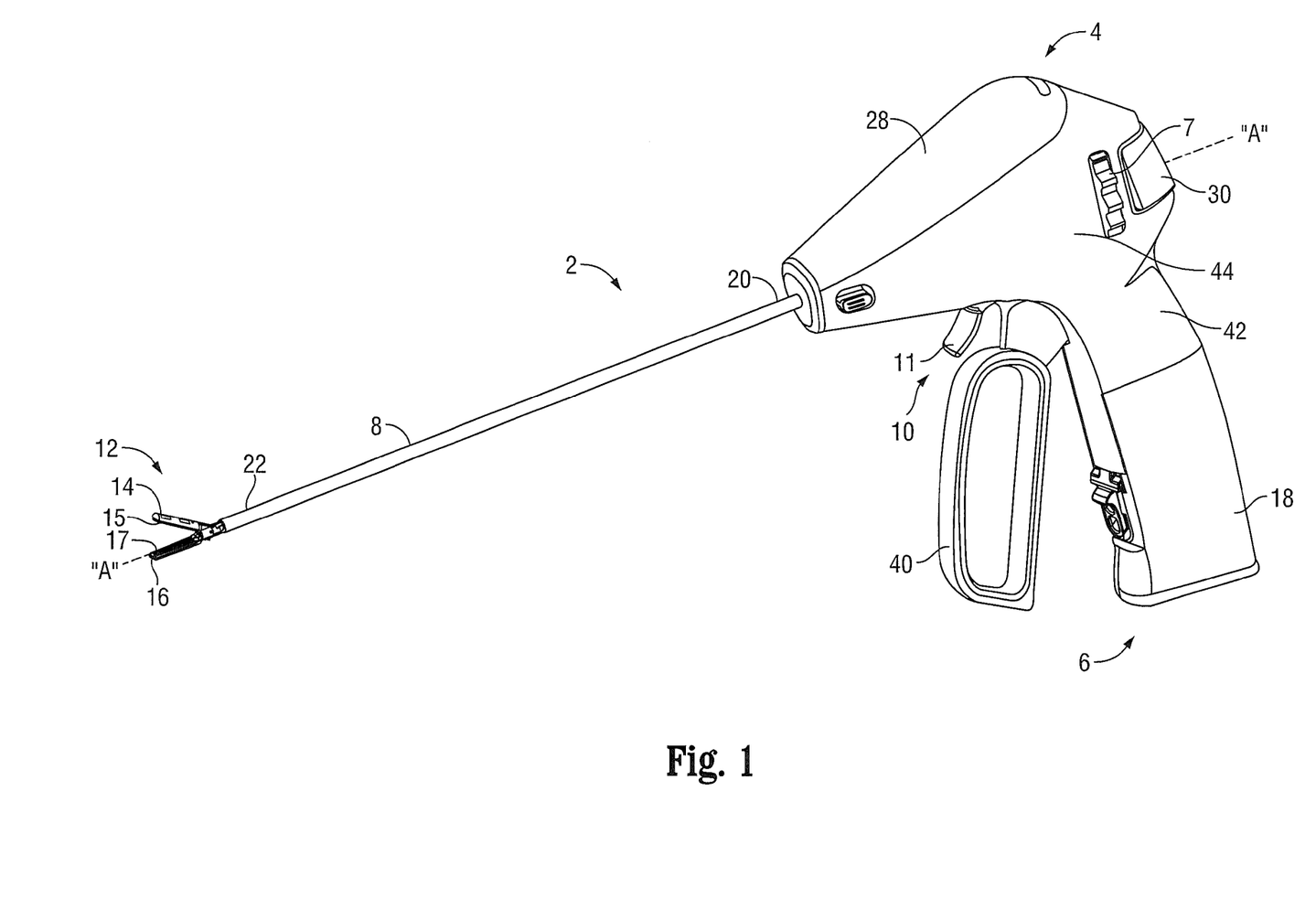
FIG. 1 is a side, perspective view of a battery-powered surgical instrument configured for use in accordance with the present disclosure.
Figure 2:
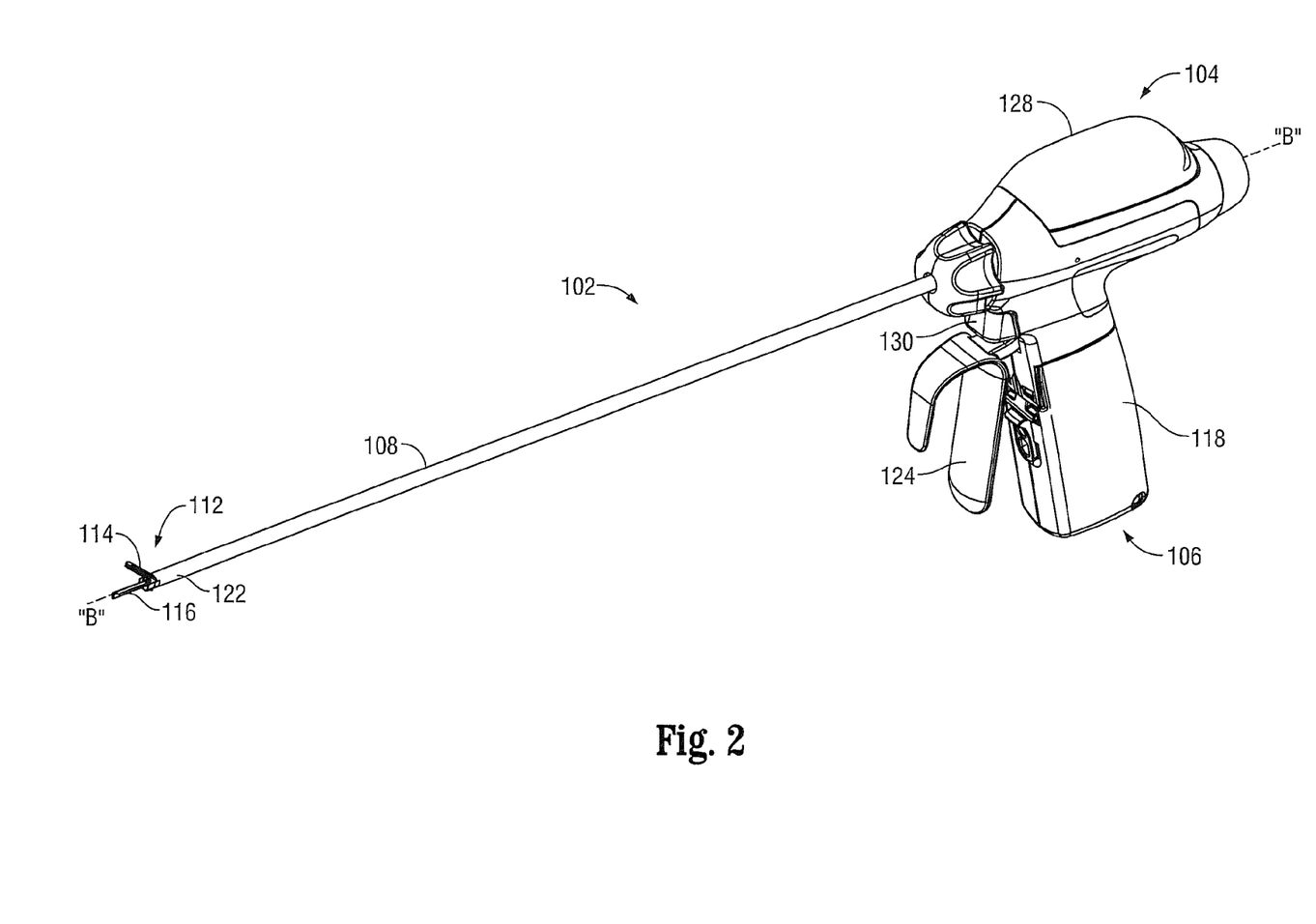
FIG. 2 is a side, perspective view of another battery-powered surgical instrument configured for use in accordance with the present disclosure.

Referring now to FIGS. 1 and 2, FIG. 1 depicts a battery-powered electrosurgical instrument 2 and FIG. 2 depicts a battery-powered ultrasonic surgical instrument 102. For the purposes herein, either an electrosurgical instrument, e.g., instrument 2, an ultrasonic surgical instrument, e.g., instrument 102, or any other suitable battery-powered device, e.g., surgical instruments, powered tools, electronics, etc., may be utilized in accordance with the present disclosure. Obviously, different considerations apply to each particular type of device, however, the features and aspects of the present disclosure are equally applicable to, and remain generally consistent with respect to any suitable battery-powered device. For the purposes herein, electrosurgical instrument 2 and ultrasonic surgical instrument 102 are generally described.

Referring to FIG. 1, electrosurgical instrument 2, shown configured as an electrosurgical forceps, generally includes a housing 4, a battery assembly 18, an electrosurgical generator assembly 28, a handle assembly 6, a rotating assembly 7, a shaft 8, a trigger assembly 10, a drive assembly (not shown), and an end effector assembly 12. End effector assembly 12 operatively connects to handle assembly 6 via the drive assembly (not shown) for imparting movement of one or both of jaw members 14, 16 of end effector assembly 12 between a spaced-apart position and an approximated position for grasping tissue therebetween.

With continued reference to FIG. 1, shaft 8 is coupled to housing 4 at proximal end 20 thereof and extends distally from housing 4 to define a longitudinal axis "A-A." End effector assembly 12, including jaw members 14 and 16, is disposed at a distal end 22 of shaft 8. End effector assembly 12 is shown configured as a unilateral assembly wherein jaw member 16 is fixed relative to shaft 8 and jaw member 14 is pivotable relative to jaw member 16 and shaft 8 between the spaced-apart position and the approximated position. However, this configuration may be reversed, e.g., wherein jaw member 14 is fixed relative to shaft 8 and jaw member 16 is pivotable relative to jaw member 14 and shaft 8. Alternatively, end effector assembly 12 may be configured as a bilateral assembly, e.g., wherein both jaw member 14 and jaw member 16 are pivotable relative to one another and shaft 8 between the spaced-apart and approximated positions.

Electrosurgical instrument 2 may be configured as a bipolar instrument. That is, each of jaw members 14, 16 may include a respective seal plate 15, 17 that is configured to function as an active (or activatable) and/or return electrode. Each seal plate 15, 17 is electrically coupled to generator assembly 28 via one or more electrical leads (not shown) that extend from generator assembly 28, through shaft 8, eventually coupling to one or both of seal plates 15, 17. However, forceps 2 may alternatively be configured as a monopolar instrument.

Handle assembly 6 includes a moveable handle 40 that is movable relative to fixed handle portion 42 for moving jaw members 14, 16 of end effector assembly 12 between the spaced-apart and approximated positions. Rotating assembly 7 rotatable in either direction about longitudinal axis "A-A" to rotate shaft 8 and, thus, end effector assembly 12 about longitudinal axis "A-A." Trigger assembly 10 is in operable communication with a knife assembly (not shown) including a knife (not shown) that is selectively translatable between jaw members 14, 16 to cut tissue grasped therebetween, e.g., upon actuation of trigger 11 of trigger assembly 10.

With continued reference to FIG. 1, housing 4 is configured to releasably engage electrosurgical generator assembly 28 and battery assembly 18 therein and/or therein. Generator assembly 28 is releasably engagable with body portion 44 of housing 4, while battery assembly 18 is releasably engagable with fixed handle portion 42 of housing 4. More specifically, battery assembly 18 is configured to engage fixed handle portion 42 of housing 4 and such that battery assembly 18 functions as a stationary handle and provides a gripping surface for the user. Generator assembly 28 releasably engages body portion 44 of housing 4 and may be selectively removable therefrom either in connection with removal of battery assembly 18 or independently thereof. When electrosurgical instrument 2 is assembled, generator assembly 28 is disposed in operable communication with battery assembly 18 to provide electrosurgical energy at one or more suitable frequencies to end effector 12 for electrosurgically treating tissue, e.g., to seal tissue. In particular, generator assembly 28 may include electronics that convert the electrical energy from battery assembly 18 into an RF energy waveform to energize one or both of jaw members 14, 16. That is, generator assembly 28 may be configured to transmit RF energy to seal plate 15 of jaw member 14 and/or seal plate 17 of jaw member 16 to seal tissue. The internal components of generator assembly 28 will be described below. Activation switch 30 disposed on housing 4 is selectively activatable for enabling generator assembly 28 to generate and subsequently transmit RF energy to seal plate 15 and/or seal plate 17 of jaw members 14, 16, respectively.

Referring now to FIG. 2, ultrasonic instrument 102 includes components similar to that of electrosurgical instrument 2 (FIG. 1), namely, a housing 104, a battery assembly 118, a generator assembly 128, a handle assembly 106, a shaft 108, and an end effector assembly 112. Accordingly, only the difference between ultrasonic instrument 102 and bipolar forceps 2 (FIG. 1) will be described hereinbelow for purposes of brevity.

Housing 104 is configured to releasably engage ultrasonic generator assembly 128 and battery assembly 118 therein or thereon. Shaft 108 extends distally from housing 104 to define longitudinal axis "B-B" and includes end effector assembly 112 disposed at distal end 122 thereof. One of jaw members, e.g., jaw member 114, of end effector assembly 112 is movable, upon actuation of moveable handle 124, between an open position and a clamping position for grasping between the jaw members 114, 116. The other jaw member, e.g., jaw member 116, serves as an active or oscillating ultrasonic blade that is selectively activatable to seal tissue grasped between jaw members 114, 116.

Generator assembly 128 includes a transducer (not shown) configured to convert electrical energy provided by battery assembly 118 into mechanical energy that produces motion at the end of a waveguide, e.g., at jaw member 116. More specifically, generator assembly 128 is configured to convert the electrical energy provided by battery assembly 118 into a high voltage AC waveform that drives the transducer (not shown). When the transducer (not shown) and the waveguide are driven at their resonant frequency, mechanical, or ultrasonic motion is produced at jaw member 116 for sealing tissue grasped between jaw members 114, 116. Further, an activation button 130 disposed on housing 104 is selectively activatable to operate instrument 102 in two modes of operation: a low-power mode of operation and a high-power mode of operation.

Turning now to FIGS. 3A-6, generator assembly 28 of electrosurgical instrument 2 (FIG. 1) is shown and described, although the present disclosure is similarly applicable to battery assembly 18 of electrosurgical instrument 2 (FIG. 1), generator assembly 128 or battery assembly 118 of ultrasonic instrument 102 (see FIG. 2), or any other suitable component of a battery-powered device that includes an internally mounted visual indicator. However, for purposes of simplicity and consistency, exemplary embodiments will be described hereinbelow with reference to generator assembly 28 of electrosurgical instrument 2 (FIG. 1) only.

With continued reference to FIGS. 3A-6, generator assembly 28 includes an outer housing 210, an inner enclosure 220, internal electronics 230 including a printed circuit board (PCB) substrate 240, and an electrical contact member 250. Internal electronics 230 and, more specifically, PCB substrate 240, is mounted within inner enclosure 220, which may be a thixoformed magnesium housing that functions as a heat sink to absorb heat produced by internal electronics 230, thereby maintaining internal electronics 230 at an acceptable temperature. Alternatively, inner enclosure 220 may be formed in any other suitable fashion and/or from any other suitable material(s) to function as a heat sink or for any other suitable purpose. Outer housing 210 surrounds inner enclosure 220 and establishes a seal about inner enclosure 220 and internal electronics 230 to function as moisture barrier inhibiting the ingress of moisture, i.e., water vapor, into generator assembly 28. Inner enclosure 220 and outer housing 210 each define an elongated aperture 222, 212, respectively, extending therethrough, the importance of which will be described below. Apertures 222, 212 may be formed within inner enclosure 220 and/or outer housing 210, respectively, during molding of the respective components or via any other suitable process. Further, a lens 214 is mounted within elongated aperture 212 of housing 210 so as to maintain the seal established by housing 210 and to facilitate visualization of light emitted from LED 260, as will be described in greater detail below. Lens 214 may be a polycarbonate lens having a refractive index of about 1.60, although any other suitable lens may also be provided.

PCB substrate 240 of generator assembly 28 include energy-generating components, e.g., electrosurgical energy-generating components, and control components that facilitate the conversion of electrical energy provided from battery assembly 18 (FIG. 1) into an RF energy waveform to energize one or both of jaw members 14, 16 of end effector assembly 12 (FIG. 1). A visual indicator, e.g., an LED 260, is mounted on PCB substrate 240. LED 260 may be any suitable LED, e.g., a surface-mounted (SMT) LED mounted on PCB substrate 240. LED 260 functions to indicate, e.g., via turning on/off, changing color, flashing, changing brightness, etc., one or more conditions or states of generator assembly 28 or surgical instrument 2 (FIG. 1). Electrical contact member 250 serves as the electrical communication interface between internal electronics 230 of generator assembly 28 and battery assembly 18 (FIG. 1) and surgical instrument 2 (FIG. 1) upon engagement of generator assembly 28 with body portion 44 of housing 4 of surgical instrument 2 (FIG. 1).

Referring still to FIGS. 3A-6, as mentioned above, inner enclosure 220 and outer housing 210 each define an elongated aperture 222, 212, respectively, extending therethrough. Elongated apertures 212, 222 are generally aligned with one another to form an elongated passageway 270 extending from the interior of generator assembly 28 to the exterior thereof through inner enclosure 220 and outer housing 210. LED 260 is mounted on PCB substrate 240 adjacent an interior end 272 of passageway 270. Lens 214 is mounted within outer housing 210 adjacent an exterior end 274 of passageway 270 and extends transversely across a top portion of generator assembly 28. As such, and as will be described in greater detail below, light emitted from LED 260 can be channeled through elongated passageway 270 to lens 214, thus allowing light emitted from the internally-displaced LED 260 to be visualized from the exterior of generator assembly 28 across relatively wide front-to-back and side-to-side viewing angles $\theta_1$ and $\theta_2$, respectively (see FIGS. 3A and 3B, respectively). Further, elongated passageway 270 and lens 214 may be positioned at or adjacent a longitudinal apex portion 29a (see FIG. 3A) and/or a transverse apex portion 29b (see FIG. 3B) of generator assembly 28 so as to maximize the front-to-back and side-to-side viewing angles $\theta_1$ and $\theta_2$, respectively (see FIGS. 3A and 3B, respectively) of light emitted from LED 260. However, it is also contemplated that elongated apertures 212, 222 may extend in any suitable direction and/or be disposed in any suitable position, depending on a particular purpose and/or configuration of the device (or component thereof) being used.

Figure 3A:
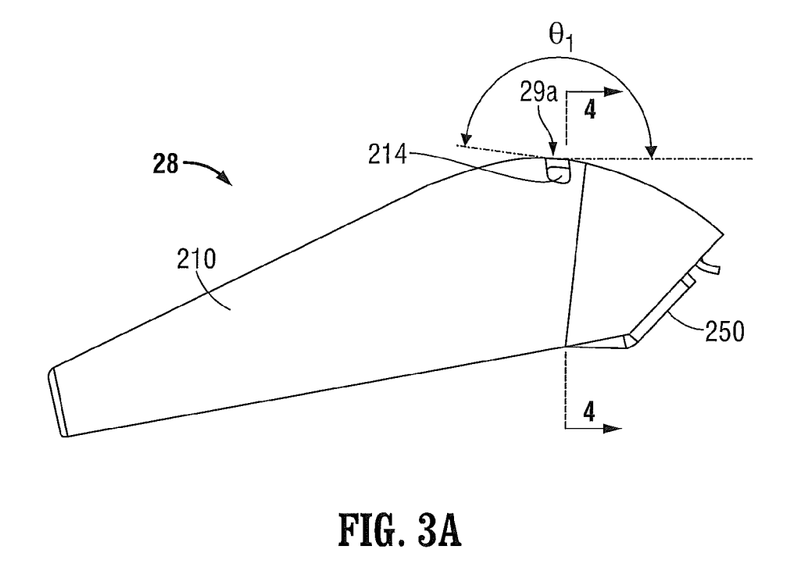
FIG. 3A is a side view of a generator assembly of the surgical instrument of FIG. 1.
Figure 3B:
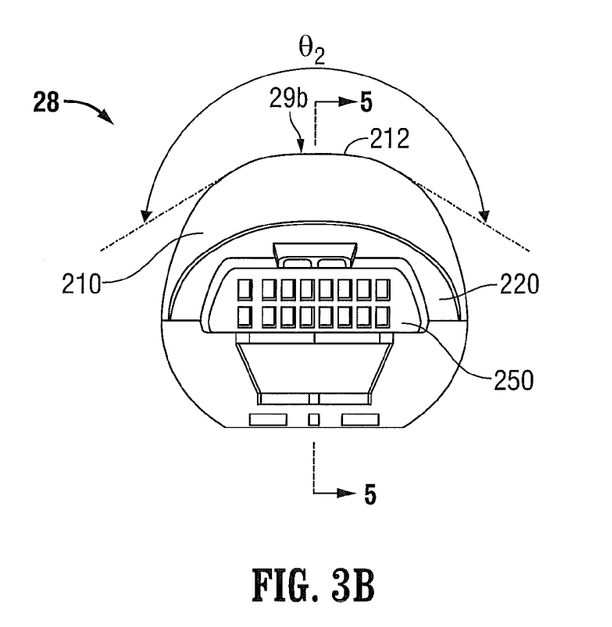
FIG. 3B is a rear view of the generator assembly of FIG. 3A.
Figure 4:
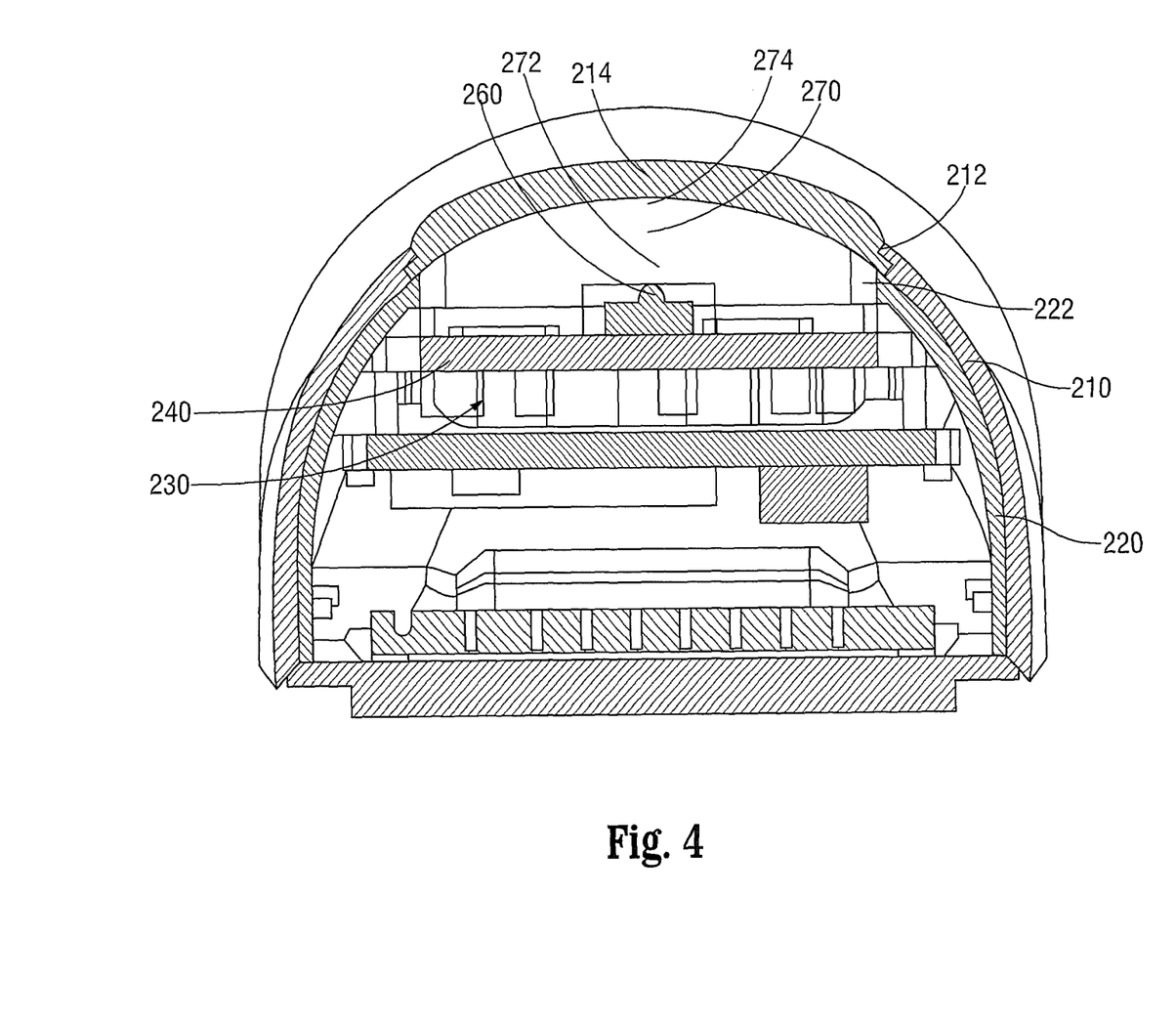
FIG. 4 is a transverse, cross-sectional view of the generator assembly of FIG. 3A taken along section line 4-4 of FIG. 3A.
Figure 5:
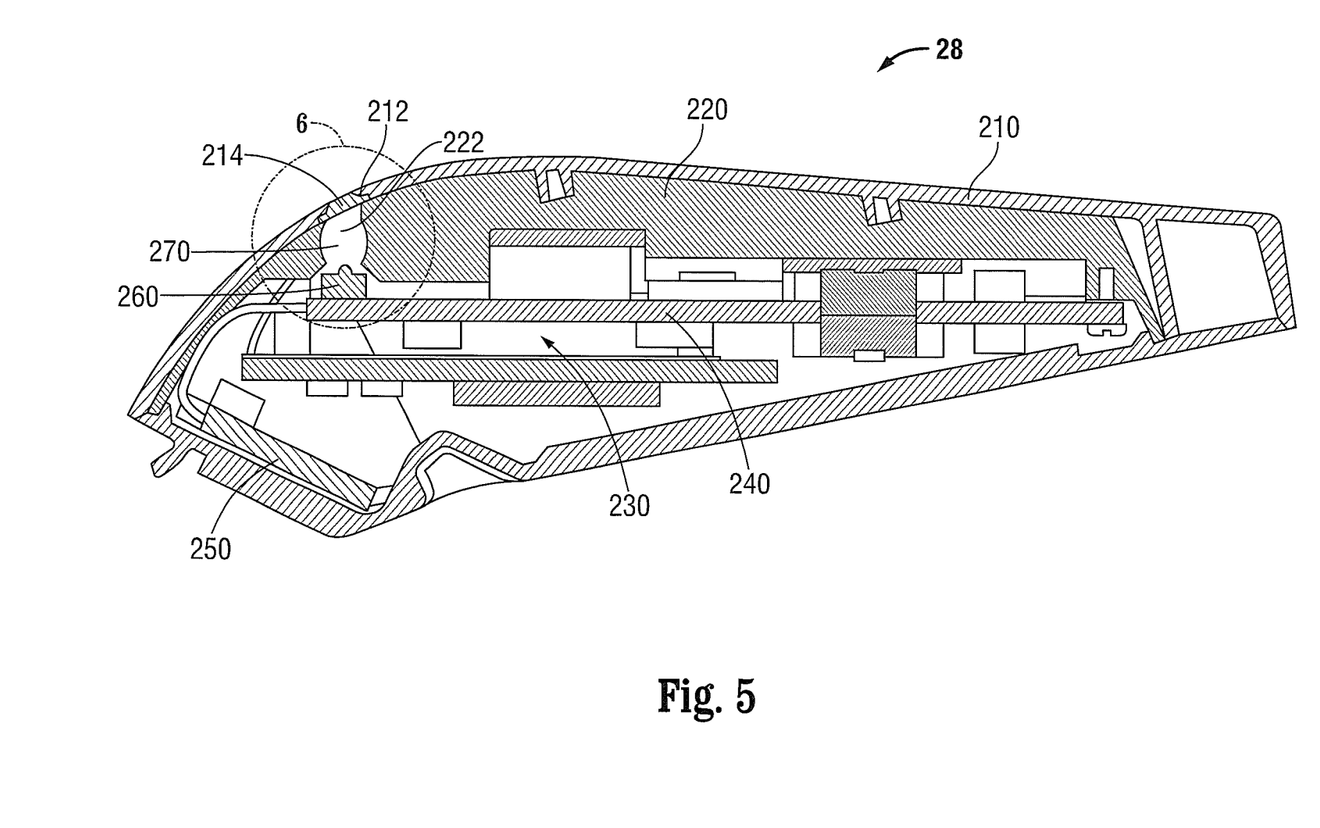
FIG. 5 is a longitudinal, cross-sectional view of the generator assembly of FIG. 3A taken along section line 5-5 of FIG. 3B.
Figure 6:
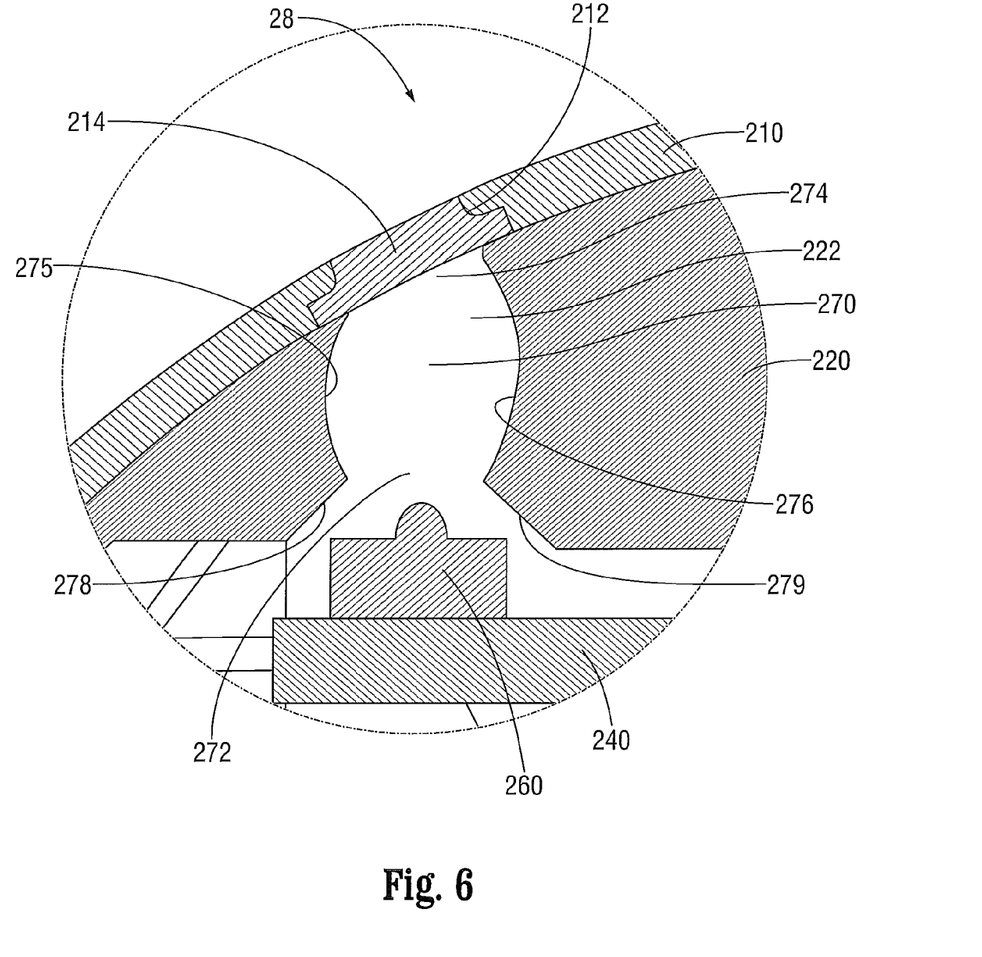
FIG. 6 is an enlarged view of the area of detail indicated as "6" in FIG. 5.

With particular reference to FIG. 6, due to the configuration of generator assembly 28, wherein LED 260 is mounted on PCB substrate 240, which is disposed within both inner enclosure 220 and outer housing 210, LED 260 is necessarily internally-displaced from lens 214 and the exterior of generator assembly 28. More specifically, outer housing 210 may define a thickness, in the vicinity of LED 260, of about 0.04 inches (1.0 mm), while inner enclosure 220 may define a thickness, in the vicinity of LED 260, of about 0.28 inches (7.1 mm), although other thicknesses are also contemplated. As such, LED 260 is internally-displaced from lens 214 a distance of at least about 0.32 inches (8.1 mm). As mentioned above, elongated apertures 212, 222 defined through outer housing 210 and inner enclosure 220, respectively, cooperate to define elongated passageway 270, through which light emitted from LED 260 is channeled to lens 214 for visualization from the exterior of generator assembly 28. The elongated configurations of passageway 270 and lens 214 allow for a relatively wide side-to-side viewing angle $\theta_2$ (FIG. 3B). However, as can be appreciated, requiring that the light emitted by LED 260 travel through the relatively narrow elongated passageway 270 prior to reaching lens 214 limits the front-to-back viewing angle $\theta_1$ from which light emitted from LED 260 can be visualized from the exterior of generator assembly 28. The width of lens 214 (in the narrow direction) may be about 0.1 inches (2.5 mm), although other widths are also contemplated.

In order to allow for a relatively wide longitudinal viewing angle $\theta_1$ despite the fact that LED 260 is internally-displaced from lens 214 and the exterior of generator assembly 28 and the fact that passageway 270 defines a relatively narrow configuration, inner enclosure 220 (and/or outer housing 210) is configured such that the elongated aperture 222 thereof, which defines at least a portion of passageway 270, includes reflecting/channeling features that reflect and channel light emitted from LED 260 through passageway 270 to lens 214 to maximize the front-to-back viewing angle $\theta_1$ from the exterior of generator assembly 28.

The above-mentioned reflecting/channeling features may include concave surfaces 275, 276 of inner enclosure 220 that define passageway 270 in the transverse direction (as shown), although other configurations are also contemplated. Forming passageway 270 via the concave surfaces 275, 276 of inner enclosure 220 allows light that is reflected off surfaces 275, 276 and received by lens 214 to have greater angles of incidence, thus allowing for an increased front-to-back viewing angle $\theta_1$ without the need to substantially alter the width of elongated aperture 222, which may reduce the overall effectiveness of outer housing 210 and/or inner enclosure 220, e.g., the moisture barrier and/or heat sinking effects thereof. Additionally or alternatively, the inner corners 278, 279 of inner enclosure 220 that define the interior end 272 of passageway 270 may be chamfered so as to allow light emitted from LED 260 to have greater angles of incidence on surfaces 275, 276 which, in turn, allows for greater angles of incidence on lens 214, likewise allowing for an increased front-to-back viewing angle $\theta_1$ without the need to substantially alter the width of elongated aperture 222. It has been found that, using the above-noted dimensions and configuration, a front-to-back viewing angle $\theta_1$ of greater than 170 degrees, e.g., about 174 degrees, can be achieved, while a side-to-side viewing angle of equal to or greater than about 220 degrees can be achieved.

While several embodiments of the disclosure have been shown in the drawings, it is not intended that the disclosure be limited thereto, as it is intended that the disclosure be as broad in scope as the art will allow and that the specification be read likewise. Therefore, the above description should not be construed as limiting, but merely as exemplifications of particular embodiments. Those skilled in the art will envision other modifications within the scope and spirit of the claims appended hereto.

What is claimed is:

1. An assembly for use with a surgical device, comprising:
   an enclosure defining a passageway extending from an interior to an exterior thereof; and
   a visual indicator mounted within the interior of the enclosure adjacent the passageway, the visual indicator configured to emit light,
   wherein the passageway is at least partially defined by one of a concave surface and a chamfered portion of the enclosure to facilitate the passage of light emitted by the visual indicator through the passageway and to the exterior of the enclosure to increase the external viewing angle of the light emitted from the visual indicator.

2. The assembly according to claim 1, further comprising an outer housing disposed about the enclosure, the outer housing including an aperture positioned adjacent the passageway to permit passage of light emitted by the visual indicator therethrough for visualization from an exterior of the outer housing.

3. The assembly according to claim 2, further comprising a lens disposed within the aperture of the outer housing, the light emitted by the visual indicator configured for passage through the lens for visualization from the exterior of the outer housing.

4. The assembly according to claim 1, wherein the visual indicator is an LED.

5. The assembly according to claim 1, further comprising electronic circuitry mounted within the interior of the enclosure, the visual indicator mounted on the electronic circuitry.

6. The assembly according to claim 5, wherein the electronic circuitry is disposed on a printed circuit board.

7. The assembly according to claim 5, wherein the enclosure functions as a heat sink to absorb heat emitted by the electronic circuitry.

8. The assembly according to claim 1, wherein the passageway is at least partially defined by at least one concave surface of the enclosure and at least one chamfered portion of the enclosure.

9. The assembly according to claim 1, wherein a thickness of the enclosure is at least about three times greater than a narrow width of the passageway.

10. The assembly according to claim 1, wherein the visual indicator is displaced from the exterior of the enclosure a distance that is at least about three times greater than a narrow width of the passageway.

11. The assembly according to claim 1, wherein a combined thickness of the inner enclosure and outer housing is at least about three times greater than a narrow width of the passageway.

12. The assembly according to claim 1, wherein the visual indicator is displaced from the exterior of the outer housing a distance that is at least about three times greater than a narrow width of the passageway.

13. The assembly according to claim 12, wherein the external viewing angle of the light emitted from the visual indicator in a direction of the narrow width of the passageway is at least about 170 degrees.

14. An assembly for use with a surgical device, comprising:
   an outer housing defining a first aperture extending therethrough;
   an inner enclosure defining a second aperture therethrough, the first and second apertures cooperating to define a passageway extending from an interior of the inner enclosure to an exterior of the outer housing; and
   a visual indicator mounted within the interior of the inner enclosure adjacent the passageway, the visual indicator configured to emit light,
   wherein the passageway is at least partially defined by one of a concave surface and a chamfered portion of the inner enclosure to facilitate the passage of light emitted by the visual indicator through the passageway and to the exterior of the outer housing to increase the external viewing angle of the light emitted from the visual indicator.

15. The assembly according to claim 14, further comprising a lens disposed within the aperture of the outer housing, the light emitted by the visual indicator configured for passage through the lens for visualization from the exterior of the outer housing.

16. The assembly according to claim 14, wherein the visual indicator is an LED.

17. The assembly according to claim 14, further comprising electronic circuitry mounted within the interior of the inner enclosure, the visual indicator mounted on the electronic circuitry.

18. The assembly according to claim 17, wherein the inner enclosure functions as a heat sink to absorb heat emitted by the electronic circuitry.

19. The assembly according to claim 17, wherein the outer housing functions as a moisture barrier to inhibit moisture from reaching the electronic circuitry.

20. The assembly according to claim 14, wherein the passageway is at least partially defined by at least one concave surface of the inner enclosure and at least one chamfered portion of the inner enclosure.

\* \* \* \* \*